United States Patent
Lu

(10) Patent No.: US 6,682,930 B1
(45) Date of Patent: Jan. 27, 2004

(54) TRIPLEX FORMING OLIGONUCLEOTIDES AND THEIR USE IN ANTI-HBV

(75) Inventor: Changde Lu, Shanghai (CN)

(73) Assignee: Shanghai Institute of Biochemistry, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 09/529,812

(22) PCT Filed: Oct. 19, 1998

(86) PCT No.: PCT/CN98/00248

§ 371 (c)(1),
(2), (4) Date: Jul. 24, 2000

(87) PCT Pub. No.: WO99/20641

PCT Pub. Date: Apr. 29, 1999

(30) Foreign Application Priority Data

Oct. 21, 1997 (CN) ........................................ 97106667 A

(51) Int. Cl.[7] ........................ C07H 21/04; C12Q 01/68; C12N 15/85; C12N 15/86; C12P 19/34
(52) U.S. Cl. ........................ 435/375; 435/6; 435/91.1; 435/325; 536/23.1; 536/24.5; 536/24.3; 536/24.31; 536/24.33
(58) Field of Search ........................ 435/6, 91.1, 91.3, 435/325, 375; 536/23.1, 23.2, 24.5, 24.3, 24.31, 24.33

(56) References Cited

U.S. PATENT DOCUMENTS

| | | | |
|---|---|---|---|
| 5,556,956 A | 9/1996 | Roy et al. | 536/24.1 |
| 5,739,308 A | 4/1998 | Kandimalla et al. | 536/24.5 |

FOREIGN PATENT DOCUMENTS

| | | |
|---|---|---|
| CN | 97 1 06495.4 | 6/1997 |
| WO | 95/19433 | 7/1995 |
| WO | 96/39502 | 12/1996 |
| WO | 96/40710 | 12/1996 |
| WO | 97/03211 | 1/1997 |

OTHER PUBLICATIONS

Lyamichev et al.; "Structures of Homopurine–Homopyrimidine Tract in Superhelical DNA"; Journal of Biomolecular Structure and Dynamics; vol. 3, No. 4; 1986; pp. 667–669.

Htun et al.; "Topology and Formation of Triple–Stranded H–DNA"; Research Articles; vol. 243; Mar. 24, 1989; pp. 1571–1576.

Moser et al.; "Sequence–Specific Cleavage of Double Helical DNA by Triple Helix Formation" Research Articles; vol. 238; Oct. 30, 1978; pp. 645–650.

Cooney et al.; "Site–Specific Oligonucleotide Binding Represses Transcription of the Human c–mpc Gene in Vitro"; Science; vol. 241; Jul. 22, 1988; pp. 456–459.

Horne et al.; Recognition of Mixed–Sequence Duplex DNA by Alternate–Stand Triple–Helix Formation; J. Am. Chem. Soc.; vol. 112; 1990; pp. 2435–2437.

Tu et al; "Inhibition of Gene Expression by Triple Helix Formation in Hepatoma Cells"; The Journal of Biological Chemistry; vol. 270, No. 47; Nov. 1995; pp. 28402–28407.

Orson et al; "Oligonucleotide Inhibition of IL2Rα mRNA Transcription by Promoter Region Collinear Triplex Formation in Lymphocytes"; Nucleic Acids Research; vol. 19, No. 12; 1991; pp. 3435–3441.

Ing et al.; "In Vitro Transcription of a Progesterone–Responsive Gene is Specifically Inhibited by A Triplex–Forming Oligonucleotide"; Nucleic Acids Research; vol. 21, No. 12; 1993; pp. 2789–2796.

McShan et al.; "Inhibition of Transcription of HIV–1 in Infected Human Cells by Oligodeoxynucleotides Designed to Form DNA Triple Helices"; The Journal of Biological Chemistry; vol. 267, No. 8; Mar. 15, 1992; pp. 5712–5721.

Postel et al.; "Evidence that a Triplex–Forming Oligodeoxyribonucleotide Binds to The c–myc Promoter in HeLa Cells, Thereby Reducing c–myc mRNA Levels"; Proc. Natl. Acad. Science USA; vol. 88; Sep. 1991; pp. 8227–8231.

Larsen et al.; "An Altered DNA Conformation Detected by S1 Nuclease Occurs at Specific Regions in Active Chick Globin Chromatin"; Cell; vol. 29; Jun. 1982; pp. 609–622.

*Primary Examiner*—Karen A. Lacourciere
(74) *Attorney, Agent, or Firm*—Foley & Lardner

(57) ABSTRACT

A type of new triplex forming oligonucleotide (TFO) which can form triplex DNA when bound to two similar fragments of homopolypurine/homopolypyrimidine sequences. TFOs were designed according to the above structure to bind the DR region and pre-S gene promoter region of HBV, respectively. The 3' end of the TFOs can be monophosphorylated or otherwise chemically modified to increase their stability. Cellular experiments prove that these TFOs can be used as drugs to inhibit HBV and treat hepatitis B. TFO and antisense oligonucleotide sequences from the DR or pre-S promoter region of HBV can together bind to target RNA sequences and form a $(DNA)_2$:RNA hetero-triplex structure that results in the more efficient inhibition of HBV.

14 Claims, 7 Drawing Sheets

HBV PRE-S GENE SEQUENCE

Figure 3:
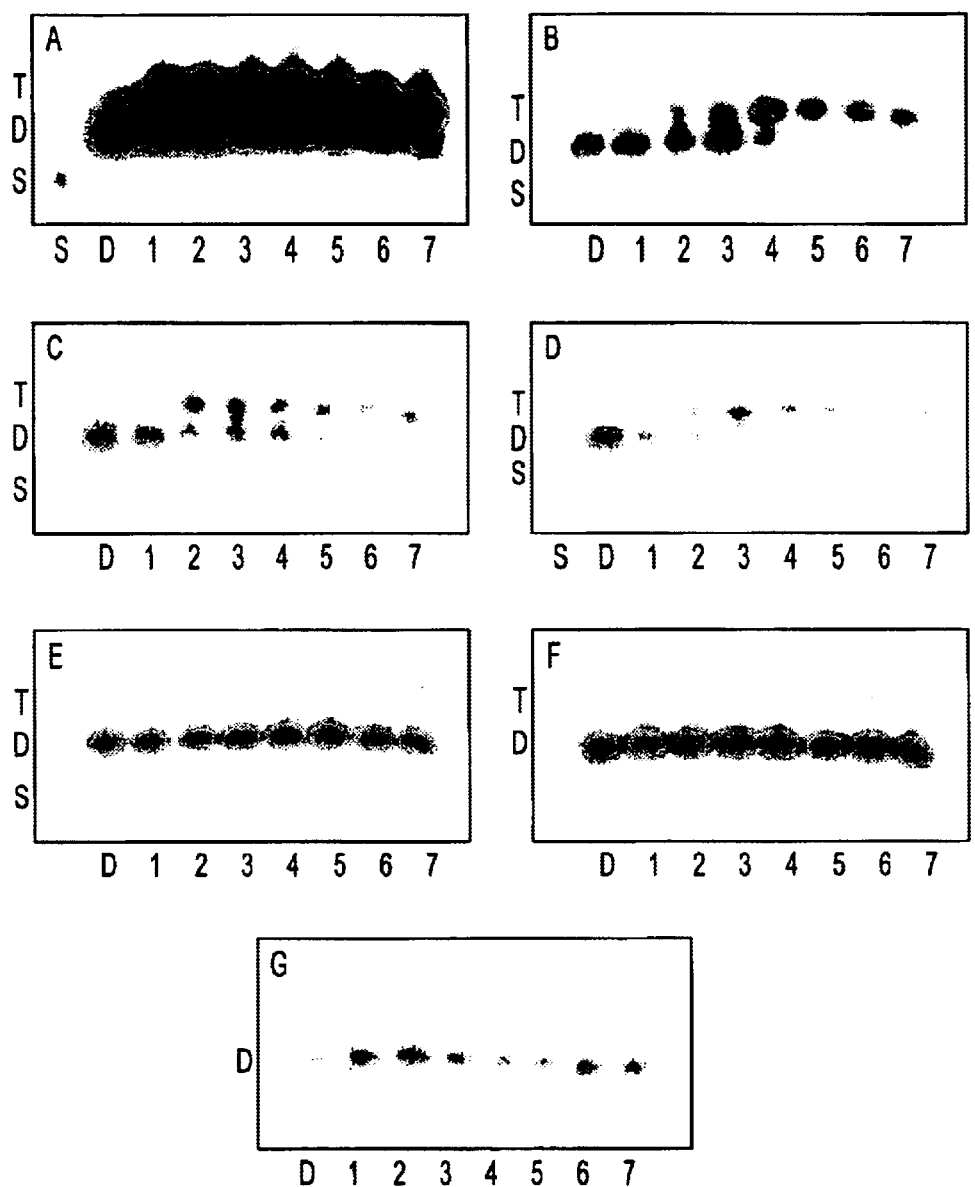

```
           3127                3143
5' CA TTC CTC CTC CTG CCT CC AC 3'      (FRAGMENT I)    21nt
3' GT AAG GAG GAG GAC GGA GG TG 5'      (FRAGMENT II)   21nt

TFO SEQUENCE
B1    5' AAG GAG GAG GAT GGA GG 3'         17nt
B2    5' AAG GAG GAG GAC GGA GG 3'         17nt
B3    5' AAG GAG GAG GAA GGA GG 3'         17nt
B4    5' AAG GAG GAG GAG GGA GG 3'         17nt
B5    5' AAG GAG GAG GA 3'   11nt
B6    5' AAG GAG GAG GAT TTT TTT T 3'      19nt
CONTROL (NC)    5'GGG ATG GAG TGG TGG AAT TCC ACA 3'    24nt
```

FIG. 1

HBV DR SEQUENCE

```
            1734                1754
5' AAT CTC CTC CCC CAA CTC CTC CCA G 3'    (FRAGMENT III)   25nt
3' TTA GAG GAG GGG GTT GAG GAG GGT C 5'    (FRAGMENT IV)    25nt

TFO SEQUENCE
B11   5' A GAG GAG GGG G 3'  11nt
B12   5' A GAG GAG GGG GAA GAG GAG GG 3'     21nt
B13   5' A GAG GAG GGG GGG GAG GAG GG 3'     21nt
B14   5' A GAG GAG GGG GCC GAG GAG GG 3'     21nt
B15   5' A GAG GAG GGG GTT GAG GAG GG 3'     21nt
```

FIG. 2

TRIPLEX FORMING OLIGONUCLEOTIDES AND THEIR USE IN ANTI-HBV

TECHNICAL SCOPE

This invention involves a new kind of triplex forming oligonucleotide (TFO), particularly a new triplex forming oligonucleotide and their derivatives that form triplex DNA with two similar homopoly purine and pyrimidine fragments. This invention also involves the application of TFO in inhibiting the hepatitis B virus.

TECHNICAL BACKGROUND

In the 1980s, it was found that in vivo double stranded DNA (dsDNA) formed by homopolypurine/homopolypyrimidine sequences can fold over, and one of the strands can then form triplex DNA with the 5'-upstream homopolypurine/homopolypyrimidine sequence of dsDNA. The other strand then becomes single stranded DNA (ssDNA). Furthermore, the triplex DNA can become involved in the regulation of gene expression (Lyamichev V I, Mirkin S M, et al., J Biomol Struct Dyn, 1986, 3: 667-9; Larsen A, Weintraub H et al., Cell, 1982, 29: 609–22; Htun H, Dahlberg J E, Science, 1989, 243: 1571–76). Triplex DNA can be also be formed by the in vitro recognition of oligonucleotides with specific target DNA. A strand of homopolypurine/homopolypyrimidine oligonucleotides can specifically recognise a complementary sequence of homopolypurines/homopolypyrimidines in dsDNA by base pair complementation, and can form a stable triplex DNA structure by linking with purine chains in dsDNA via Hoogsteen bonds or anti-Hoogsteen bonds. The oligonucleotide fragment that forms triplex DNA with dsDNA is named Triplex Forming Oligonucleotide (TFO). The formation of triplex DNA can inhibit the binding of proteins to DNA. TFO carrying a terminal EDTA-$Fe^{2+}$ to bind a specific target sequence can form triplex DNA, resulting in the targeted dsDNA being cleaved at that specific position in the triplex (Moser H. E., Dervan P. B., Science, 1987, 238: 645–50). Therefore, it is possible to inhibit gene expression at the DNA level by the formation of triplex DNA, which gives rise to the so-called Antigene Strategy.

This technology is superior to anti-sense and nuclease technologies. TFO uses a specific sequence of dsDNA as a binding site to form triplex DNA or to cleave targeted DNA at a specific location in the triplex DNA. This inhibits transcription or gene replication. Anti-sense nucleic acids and nuclease enzymes both target mRNA. They cause the inhibition of gene expression by binding with mRNA to stop translation, or by promoting the degradation of mRNA. In cells, a single copy of DNA can produce multiple copies of mRNA. Therefore, it may be more efficient at the DNA level to block gene replication or transcription. DNA replication or RNA transcription can be inhibited by two strategies based on the theory of triplex DNA formation and the rules of base pair complementarity. One strategy is to use a TFO fragment based on a promoter of a particular gene, so that it forms triplex DNA by binding to the complementary sequence of the targeted gene, thereby blocking the binding of protein to DNA. In the second strategy, a TFO fragment is designed based on a specific portion of a gene, with which it forms triplex DNA by binding to the complementary sequence of the targeted gene. This inhibits DNA replication or RNA transcription by blocking the movement of the replication-transcription complex. In 1988, Cooney and coworkers proved that the molecular-triplex DNA structure formed at the starting point of c-myc inhibits the transcription of c-myc (Cooney M., Science, 1988, 241:450–9). However, up until now, there have been very few practical applications of TFO in the inhibition of gene expression. In a review of international patents, only one such patent has been found, and this involved the application of TFO to inhibit the expression of androgen receptor gene (U.S Pat. No. 5,556,956, Sep. 17, 1996). The main reason for this lack of applications is that it is very rare to find in promoters or other particular regions of genes homopolypurine/homopolypyrimidine sequences which are long enough. The triplex DNA formed by relatively short TFOs and target dsDNA is not particularly stable or specific, therefore their ability to act as inhibitors is weak, which limits their practical application in the Antigene Strategy. There have only been a few theoretical studies on the range of target dsDNA that can form triplex DNA, but no practical applications have resulted. Horne and Dervan et al designed an alternating triplex DNA containing two fragments of homopolypurine sequences located on the two chains of dsDNA, whereby a part of the TFO sequence matches a purine chain in the double strand, and the other part of the TFO matches the other purine chain in the double strand (Home D A, Dervan P B, J. Am. Chem. Soc., 1990; 112: 2435–37).

The stability of triplex DNA has also been studied. It was found that triplex DNA could still be formed even though it contains a single mismatched base, but its stability is markedly decreased. Therefore, problems are still to be resolved in finding new TFO structures that can be used to inhibit the expression of harmful genes. There have also been studies on increasing the stability and inhibitory effect of TFO by chemical modification, including thiophosphate modification (Tu, et al., J. Biol. Chem., 1995, 270: 28402–7), a single amino acid linked to the 3'-end (Orsen F. M., et al. Nucleic Acids Res. 1991, 19: 3435–41; Postel E. H., et al. Proc. Natl. Acad. Sci. USA 1991, 88: 8827–31; McShan W. M., et al. J. Biol. Chem. 1992, 267: 5712–21), cholesterol linked to the 3'-end (Ing N. H. et al., Nucleic Acids Res., 1993, 21: 2789–96) and so on. Although the stability and inhibitory capability of TFO can be increased by chemical modification, the length of TFO is still the key factor in TFO stability.

HBV is a hepatic DNA virus that can cause acute and chronic hepatitis. Eighty percent of patients with Hepatocellular Carcinoma (HCC) have HBV infection. The relative risk of HCC in the population with chronic HBV infection increases at least 100 fold. China is a high epidemic region for hepatitis B. Eight to 10% (100 million) of the population are positive to Hepatitis B (virus) Surface Antigen (HBsAg). Hepatitis B caused by HBV and the associated HCC are one of the major health issues in the world. However, as of the present, there is still no effective therapeutic regimen in the clinic. Hence the development of TFO against HBV as a new therapeutic approach is of contemporary interest. However, as the HBV genes do not contain homopolypurine/homopolypyrimidine sequences which are long enough to be a practicable target for TFO, it is worthwhile to search for a new triplex DNA structure.

PURPOSE OF THE INVENTION

The aim of the invention is to provide a type of TFO which is able to form a triplex DNA structure with two fragments of homologous homopolypurine/homopolypyrimidine. This TFO can inhibit the expression of HBV genes and the replication of the virus. It includes two types of TFO. One can bind to two fragments of homologous homopolypurine/homopolypyrimidine in the DR region of HBV. The other binds to two fragments of homologous homopolypurine/homopolypyrimidine in the promoter region of the pre-S gene of HBV adr subtype. Their stability can also be increased by 3'-monophosphorylation or other chemical modifications. These TFOs can be used as therapeutic agents in the treatment of hepatitis B.

DETAILS

The invention provides a type of TFO which is able to form a triplex DNA structure with two fragments of homologous homopolypurine/homopolypyrimidine. The invention is based on the mechanism of triplex DNA formation and the sequences in HBV genes. It is aimed at two fragments of homologous homopolypurine/homopolypyrimidine sequences in the DR region of HBV and the promoter region of pre-S gene of HBV adr subtype. The invention involves the corresponding TFOs, as well as the synthesis on a DNA synthesiser of these TFOs and 3'-monophosphorylated TFO derivatives (see FIG. 1 and FIG. 2):

homopolypyrimidine in the DR region of HBV. Of these, the binding activity of B15 and B12 is stronger than B11, and B15 is the strongest. B5 and B11 can only bind one fragment of homologous homopolypurine/homopolypyrimidine in the promoter region of the pre-S gene of HBV adr subtype and the DR region of HBV, respectively. The binding activity of TFOs B1–B4 is stronger than B5, which explains the fact that TFOs B1–B4 can bind the two fragments of homologous homopolypurine/homopolypyrimidine in the pre-S gene of HBV.

TFO B6 is another oligonucleotide example which proves the point. In contrast with TFO B5, TFO B6 has extra eight Ts at the 3'-end, and can not bind to the second fragment of homologous homopolypurine/homopolypyrimidine. Also, it binds target sequences much more weakly than B5. Likewise, the binding activities of TFOs B15 and B12 are stronger than B11, which indicates that TFOs B15 and B12 can bind to the two fragments of homologous homopolypurine/homopolypyrimidine in the DR region of HBV. These results show that the TFOs disclosed in this invention can bind two fragments of homologous homopolypurine/homopolypyrimidine to form a new triplex

```
B1  (SEQ ID NO:1)5'      AAG GAG GAG GAT GGA GG 3'  17nt
B2  (SEQ ID NO:2)5'      AAG GAG GAG GAC GGA GG 3'  17nt
B3  (SEQ ID NO:3)5'      AAG GAG GAG GAA GGA GG 3'  17nt
B4  (SEQ ID NO:4) 5'     AAG GAG GAG GAG GGA GG 3'  17nt
B5  (SEQ ID NO:5)5'      AAG GAG GAG GA      3'     11nt
B11 (SEQ ID NO:6)    5'  AGA GGA GGG GG 3' 11nt
B12 (SEQ ID NO:7)    5'  AGA GGA GGG GGA AGA GGA GGG 3'21nt
B13 (SEQ ID NO:8)    5'  AGA GGA GGG GGG GGA GGA GGG 3 21nt
B14 (SEQ ID NO:9)    5'  AGA GGA GGG GGC CGA GGA GGG 3'21nt
B15 (SEQ ID NO:10)   5'  AGA GGA GGG GGT TGA GGA GGG 3'21nt
B1  (3'P) (SEQ ID NO:1)  5'  AAG GAG GAG GAT GGA GGp 3'           17nt
B2  (3'P) (SEQ ID NO:2)  5'  AAG GAG GAG GAC GGA GGp 3'           17nt
B3  (3'P) (SEQ ID NO:3)  5'  AAG GAG GAG GAA GGA GGp 3'           17nt
B4  (3'P) (SEQ ID NO:4)  5'  AAG GAG GAG GAG GGA GGp 3'           17nt
B5  (3'P) (SEQ ID NO:5)  5'  AAG GAG GAG GAp 3' 11nt
B11 (3'P) (SEQ ID NO:6)  5'  AGA GGA GGG GGp 3' 11nt
B12 (3'P) (SEQ ID NO:7)  5'  AGA GGA GGG GGA AGA GGA GGGp              3'21nt
B13 (3'P) (SEQ ID NO:8)  5'  AGA GGA GGG GGG GGA GGA GGGp              3'21nt
B14 (3'P) (SEQ ID NO:9)  5'  AGA GGA GGG GGC CGA GGA GGGp              3'21nt
B15 (3'P) (SEQ ID NO:10) 5'  AGA GGA GGG GGT TGA GGA GGGp              21nt
```

In order to study the binding ability of TFO to the two fragments of homologous homopolypurine/homopolypyrimidine in the DR region of HBV and the promoter region of pre-S gene of HBV adr subtype, the thermodynamic parameters of triplex DNA formation were measured using band mobility shift assays. TFOs B1–B5 can bind to the two fragments of homologous homopolypurine/homopolypyrimidine in pre-S genes of HBV. Of these, B1–B4 bind more strongly than B5, and B4 showed the strongest binding activity. TFOs B11, B12 and B15 can bind to the two fragments of homologous homopolypurine/

DNA structure. Moreover, the bases in the TFO with a strong matching capability bind the target DNA by Hoogsteen bonds or anti-Hoogsteen bonds. When the new TFOs described in this invention bind the two fragments of homologous homopolypurine/homopolypyrimidine in the DR region of HBV and the promoter region of pre-S gene of HBV adr subtype, the target dsDNA structure changes from purines to pyrimidines. Although these changes reduce the stability of triplex DNA, the stability and specificity of the binding between the extended TFO and target DNA ultimately undergoes a major increase. Thus they show stronger inhibition. This also proves that the major factor affecting the stability of triplex DNA formation is the length of the TFO.

In order to study TFO's inhibition of HBV gene expression and the inhibition of viral replication, hepatic $HepG_2$ cells transfected by a plasmid (p1.2II) containing HBV genes were used as a model for studying the effects of TFO. Plasmid (p1.2II) contains cloned HBV (adr subtype) genes 1.2 times normal length, including the full length of the HBV genome and the overlapping region 1403–1983, and which can express all of the HBV mRNA. After p1.2II transfection of HepG2 cells, intact and infectious viral particles were produced. The inhibition of HBV genes by TFO was observed using commercial kits to test the expression levels of HBsAg and HBeAg. The inhibition of HBV replication by TFO was observed by measurement of the number of copies of HBV DNA in the cells.

Given that serum and cells contain high nuclease activity, TFOs can be chemically modified so as to increase their stability. Examples of modification are thiophosphorylation, methyl-phosphorylation, 2'-O-methylation and 3'-monophosphorylation, etc. Serum mostly contains 3'→5' exonuclease activity, and this enzyme requires a nucleic acid with a 3'-OH end as a substrate. According to previous results of the inventor (refer to patent no. 97106495.4, application date: Jun. 28, 1997), 3'-monophosphorylated oligonucleotides proved to be the best derivative. After the 3'-OH of an oligonucleotide was phosphorylated, it could no longer serve as a substrate for the 3'→5' exonuclease, thereby prolonging its retention in serum and cells. Thus it could more efficiently bind target genes. The stability of 3'-phosphorylated oligonucleotides in serum is markedly higher than that of unmodified oligonucleotides, and is slightly higher than for thiophosphorylated oligonucleotides. The uptake of 3'-phosphorylated oligonucleotides by cells is also higher than for unmodified or thiophosphorylated oligonucleotides. In addition, as 3'-phosphorylated oligonucleotides do not carry any unnatural components in the modification, its metabolites exhibit no toxicity or side-effects. Therefore, 3'-phosphorylation is an even better modification method, being superior and safer.

TFOs B4(3'P) and B15(3'P), which exhibit the strongest binding to target sequences, were selected for studying the ability of TFO to inhibit the expression of HBV genes and to inhibit the replication of HBV. The results show that the TFOs synthesised in this study inhibited the expression of HBV genes and the replication of HBV DNA, thereby inhibiting the replication of hepatitis B virus. Hence, these TFOs can be used to produce drugs for the inhibition of HBV and the treatment of hepatitis B.

In addition, HBV is a type of virus in which the genes are closely packed together. Four promoter regions of the virus genes all overlap with coding regions. Moreover, the transcription products, four mRNA sequences of 3.5 kb, 2.4 kb, 2.1 kb and 0.8 kb length respectively, all share a comnmon 3'-end. The 3'-end of a 3.5 kb pre-gene RNA is the template for reverse transcription of the virus into DNA. The two target sequences disclosed by the invention are both located in the 3.5 kb pre-gene RNA. The DR region is in the 3'-end of the 3.5 kb pre-gene RNA and the pre-S gene region is in the middle of the pre-gene RNA. At the same time, adding the anti-sense sequence oligonucleotide of the DR region: AsDR 5' TCT CCT CCC CCA ACT CCT CCC 3' (SEQ ID NO: 11) or its derivatives formed $(DNA)_2$:RNA heterotriplex with TFOs B15 (or B12, B11) and their derivatives by binding to target sequences in RNA. Alternatively, adding the anti-sense sequence oligonucleotide of the pre-S region: AsPS 5' GGA GGC AGG AGG AGG AA 3' (SEQ ID NO: 12) or its derivatives formed $(DNA)_2$:RNA heterotriplex with TFOs B4 (or B1, B2, B3, B5) and their derivatives by binding to target sequences in RNA. Also, adding the anti-sense sequence oligonucleotide of the DR region: AsDR (3'P) 5' TCT CCT CCC CCA ACT CCT CCCp 3' (SEQ ID NO: 11) formed $(DNA)_2$:RNA heterotriplex with TFOs B15 (3'P) for B12 (3'P), Eu (3'P)] by binding to target sequences of RNA. Or, adding the anti-sense sequence oligonucleotide of the pre-S region: AsPS (3'P) 5' GGA GGC AGG AGG AGG AAp 3' (SEQ ID NO: 12) formed $(DNA)_2$:DNA [sic] heterotriplex with TFOs B4 (3'P) [or B1 (3'P), B2 (3'P), B5 (3'P)]. This segment of $(DNA)_2$:RNA heterotriplex sequence inhibited reverse transcription of virus into DNA by blocking the movement of the replicating machinery. This increased the effect of TFO in inhibiting the hepatitis B virus.

Thus, combining TFOs or TFO derivatives with the anti-sense sequence oligonucleotide of the same region not only inhibits transcription of HBV genes, but it can also form heterotriplexes in the target sequence of pre-RNA, which inhibits DNA reverse transcription. The end result is the more effective inhibition of HBV reproduction. Thus, TFO and its derivatives B4 (or B1, B2, B3, and B5) combined with AsPS can be used to make drugs for the inhibition of HBV and the treatment of Hepatitis B. Similarly, B15 (or B11, B12) combined with AsDR can also be used, as can the TFOs and their derivatives B4(3'P) [or B1(3'P), B2(3'P), B3(3'P), B5(3'P)] with ASPS (3'P), as well as B15(3'P) [or B11(3'P), B12(3'P)] with AsDR (3'P).

ADVANTAGES OF THE INVENTION

1. The invention provides a series of TFOs and their derivatives which form triplex DNA with the two fragments of homologous homopolypurine/homopolypyrimidine. The stability and specificity of the triplex DNA are increased by the extension of oligonucleotide length. As the TFOs form triplex DNA with the two fragments of homologous homopolypurine/homopolypyrimidine, the applicability of TFO in the Antigen Strategy is extended.

2. The invention provides a series of TFOs which can inhibit the expression of HBV genes and the reproduction of HBV. This represents a material which can directly inhibit the expression of HBV genes and the reproduction of HBV, and thereby provides a new therapeutic approach for hepatitis B.

3. The inhibition by TFO of HBV gene expression and HBV reproduction are highly specific and do not of themselves affect human cells.

4. This invention provides increased in vivo stability of the TFOs by 3'-monophosphorylation, which also markedly increases their inhibition activity. As the TFOs described in this invention do not contain any artificial components, their metabolites have no toxic side-effects in humans.

5. At the same time, adding an anti-sense oligonucleotide derived from the same region, allows it to combine with a TFO, bind target sequence RNA and form a $(DNA)_2$:RNA heterotriplex structure, which blocks the movement of the replication machinery, thereby inhibiting virus RNA reverse transcription into DNA, and increasing the anti-HBV effect of TFO.

ILLUSTRATIONS

FIG. 1. The 21 bp double strand sequence of pre-S gene (SEQ ID NOS: 13 & 14) and the custom TFO sequences (SEQ ID NOS 1–5 and 15 & 16, respectively in order of appearance).

The numbers on the top of the sequence indicate the position of the underlined bases in the HBV gene. The bases in bold italic indicate hetero-matched base pairs inserted into the gene fragments and bases inserted into the corresponding position of the TFO sequence.

FIG. 2. 25 bp double strand sequence of the HBV DR region (SEQ ID NOS 17 & 18) and the custom TFO sequences (SEQ ID NOS 6–10, respectively in order of appearance).

The numbers on the top of the sequence indicate the position of the underlined bases in the HBV gene. The bases in bold italic indicate hetero-matched base pairs inserted into the gene fragments and bases inserted into the corresponding position of the TFO sequence.

FIG. 3. PAGE analysis of the triplex DNA formed by the 21 bp double strand sequence of pre-S gene and TFOs B1–B6.

A, B, C, D, E, F, and G are the result of binding TFOs B1–B6 and control oligonucleotide (NC) with dsDNA, respectively. S, D, and T along the side of the gels indicate the positions of single strand, double strand and triplex DNA. Along the bottom of the gels: S: single strand DNA control without TFO added; D: dsDNA control without TFO added; 1–7 respectively refer to the concentration of TFO used, namely 1, 2, 3, 4, 5, 6, 7 $\mu$mol/L.

Figure 4:
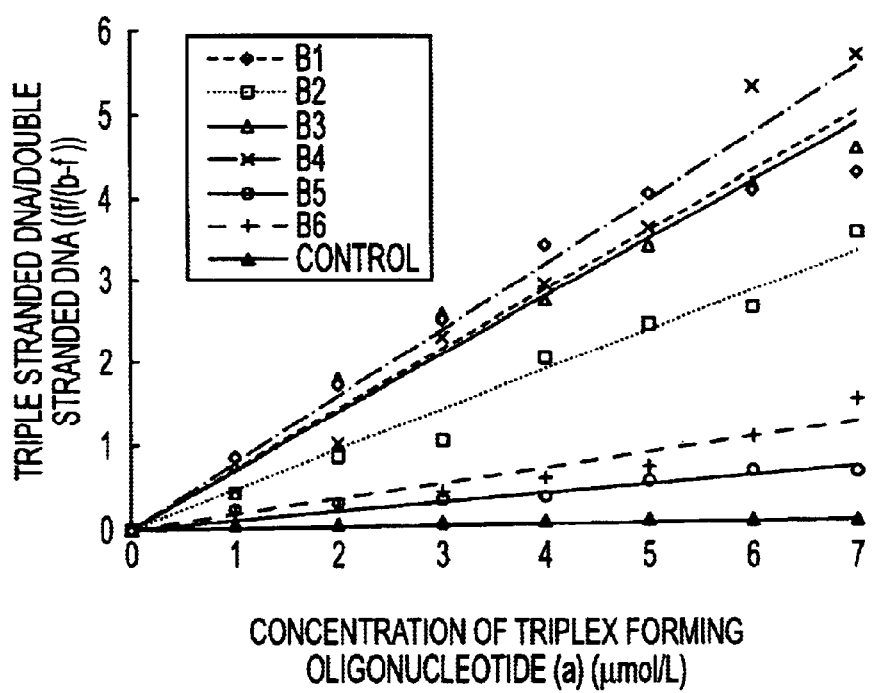

FIG. 4. The correlation curves of the ratio f/(b−f) of triplex DNA and dsDNA versus the concentration of TFO (a), when triplex DNA is formed from the 21 bp double strand sequence of pre-S gene and TFOs B1–B6.

Figure 5:
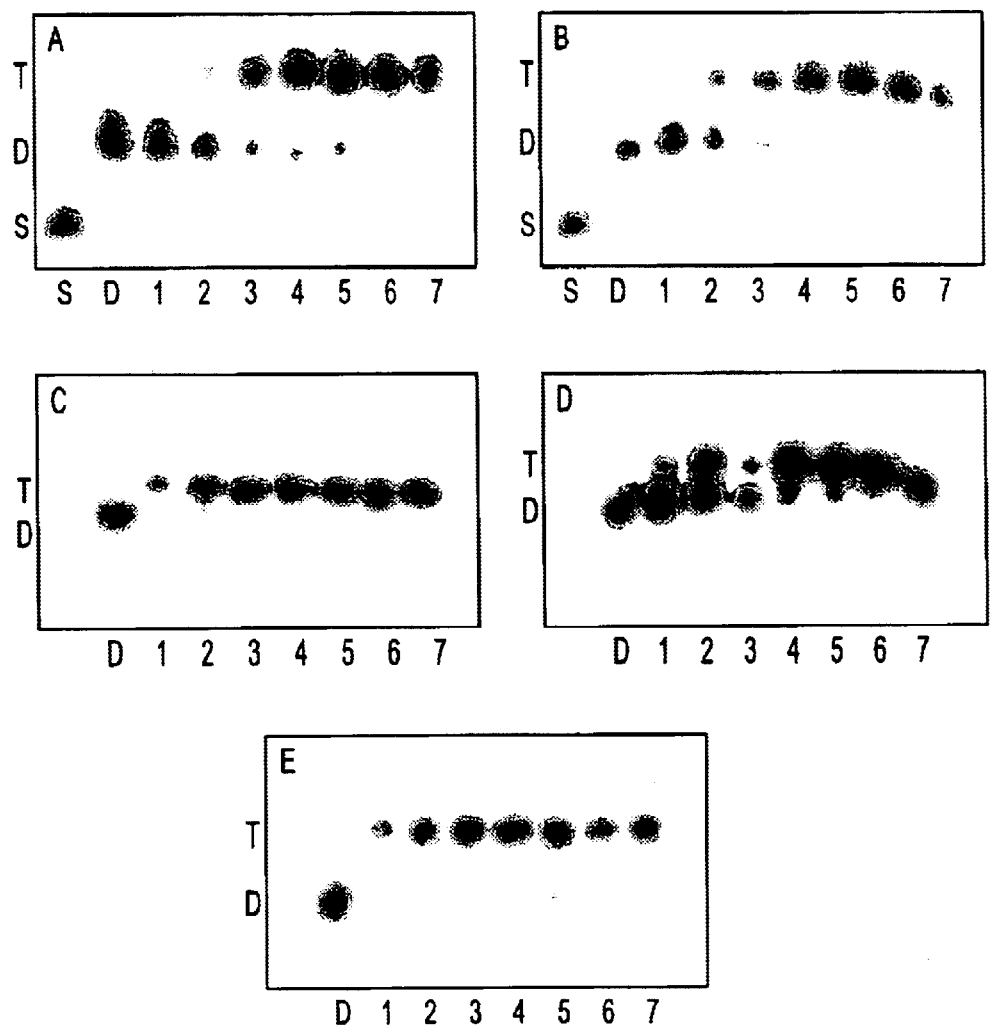

FIG. 5. PAGE analysis of the triplex DNA formed from the 25 bp double strand sequence of the HBV DR region and TFOs Bll-B15. A, B, C, D, E: the result of binding of TFOs B11–B15 with dsDNA, respectively. The abbreviations are as for FIG. 3.

Figure 6:
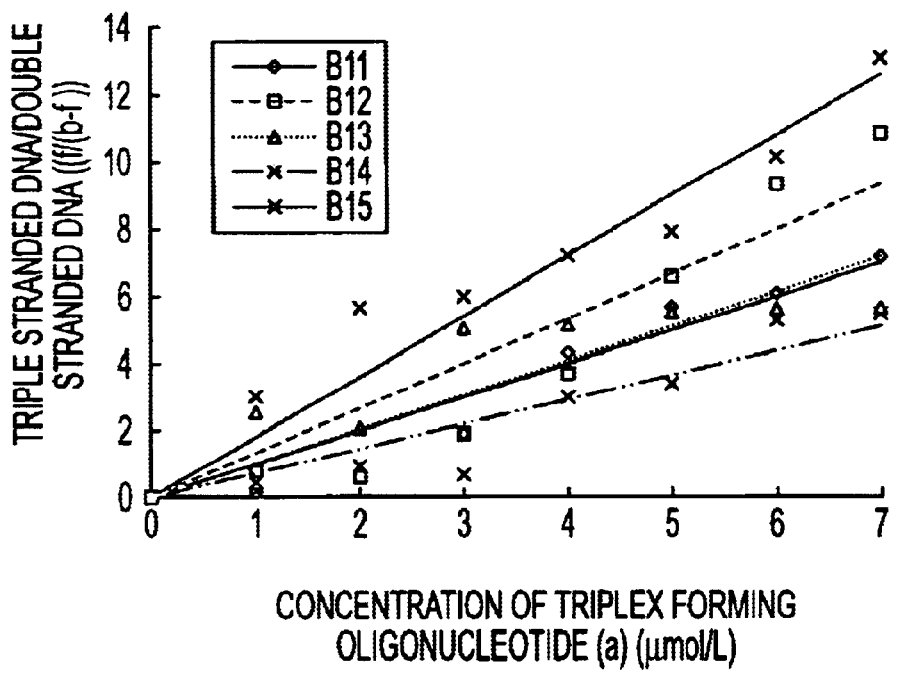

FIG. 6. The correlation curves of the ratio f/(b−f) of triplex DNA and dsDNA versus the concentration of TFO (a), when triplex DNA is formed from the 25 bp double strand sequence of HBV DR region and TFOs B11–B15.

Figure 7:
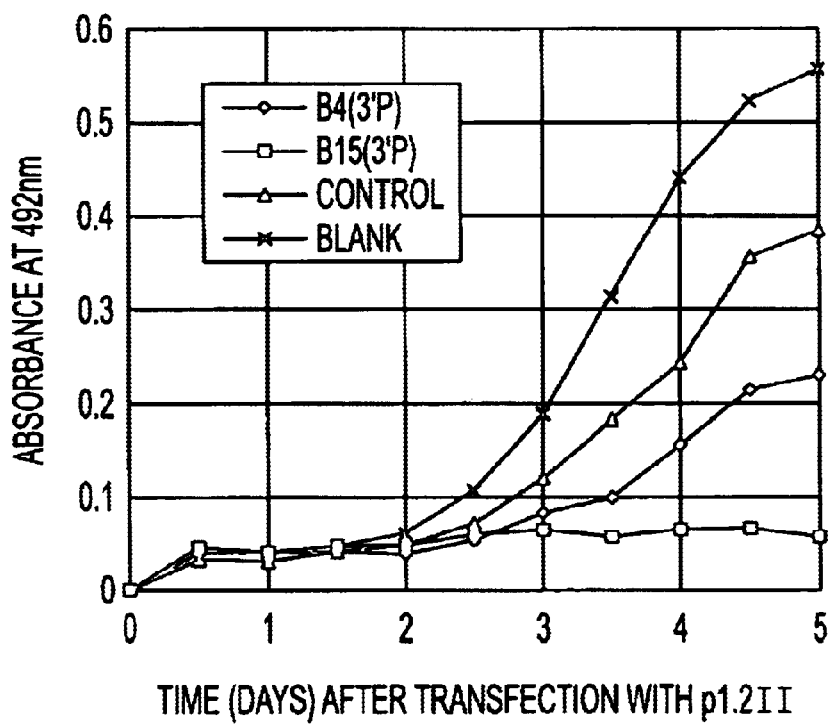

FIG. 7. Time curves for the inhibition of HBsAg expression by TFOs.

The concentration of TFO or the control deoxyoligonucleotide is 10 $\mu$mol/L. (X) No oligonucleotide added; (♦) B4(3'P) added; (■) B15(3'P) added; (▼) control deoxyoligonucleotide.

Figure 8:
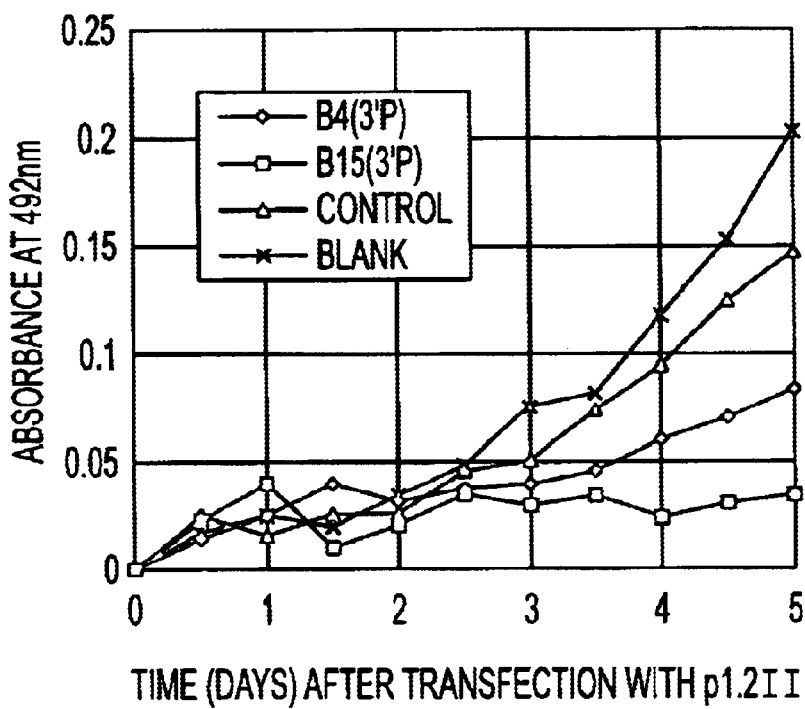

FIG. 8. Time curves for the inhibition of HBeAg expression by TFOs.

The concentration of TFO or the control deoxyoligonucleotide is 10 $\mu$mol/L. (X) No oligonucleotide added; (♦) B4(3'P) added; (■) B15(3'P) added; (▼) control deoxyoligonucleotide.

Figure 9:
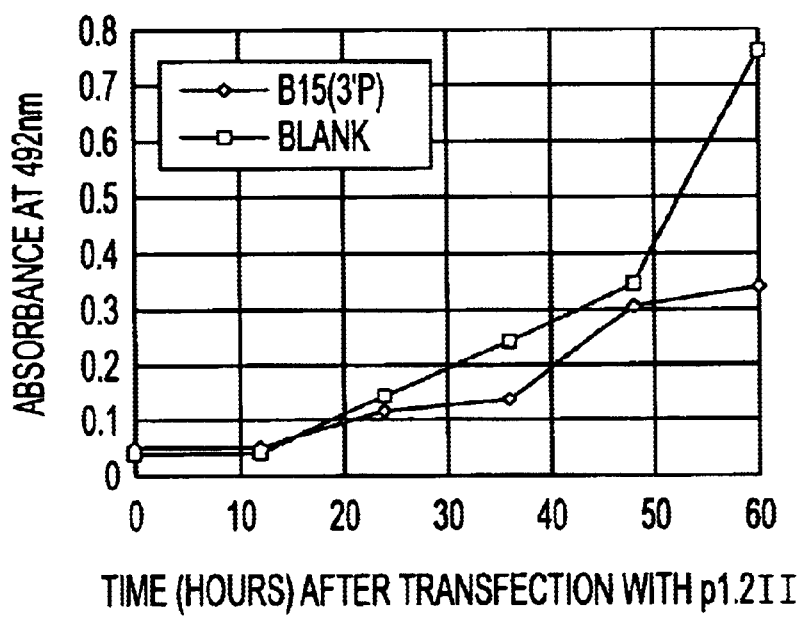

FIG. 9. Inhibition of HBsAg expression by TFO B15(3'P) in HepG$_2$ cells pre-transfected with HBV plasmid.

The concentration of TFO B15 is 10 $\mu$mol/L.

Figure 10:
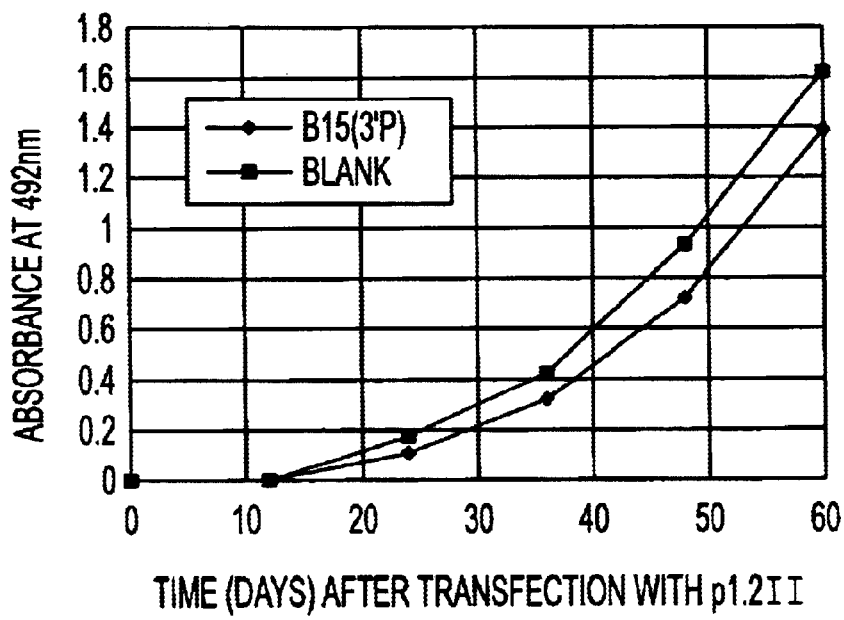

FIG. 10. Inhibition of HBeAg expression by TFO B15 (3'P) in HepG$_2$ cells pre-transfected with HBV plasmid.

The concentration of TFO B15 is 10 $\mu$mol/L.

Figure 11:
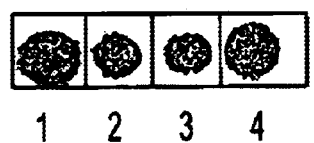

FIG. 11. Dot hybridization of HBV DNA from HepG$_2$ cells

1: no oligonucleotide; 2: add TFO B4(3'P); 3: add TFO B15(3'P); 4: add control oligonucleotide.

EXAMPLES

Example I. Design, Synthesis and Purification of TFO

I.A. Design of a TFO Fragment

A 17bp sequence located in position 3127–3143 of the HBV adr subtype nucleic acid contains almost all purines except for a cytosine in position 12 (see FIG. 1). Two complementary fragments (fragment I and fragment II) of HBV pre-S gene, a series of triplex forming oligonucleotide fragments (TFOs B1–B6) and a control oligonucleotide (NC) were synthesised according to the principles of base pair complementarity in triplex DNA. In TFOs B1–B4, the position corresponding to the cytosine in the pre-S gene fragment was taken by thymine, cytosine, adenine and guanine, respectively, so as to determine which base better matches the G.C pair, forms a more stable triple base entity, and thereby creates a triplex DNA with relatively high stability. The 11 nucleic acids at the 5'-end of TFO B6 and TFOs B1–B4 are the same, all purine-containing nucleic acids, which can form triplex DNA with the pre-S gene fragment. The eight nucleic acids at the 3'-end of TFO B6 are all T, which can not form triplex DNA with the pre-S gene fragment. By comparing the stability of triplex DNA formed by TFOs B1–B4 or TFO B6 with the pre-S gene fragment, we can assess if the 3'-end of TFO B1–B4 can form triplex DNA with the pre-S gene fragment, and so whether triplex DNA formation is interrupted by a hetero-base inserted into the homopolypurine/homopolypyrimidine sequence of dsDNA. NC is the control oligonucleotide.

In the HBV DR region of the hepatitis B virus genome, there is a 21 bp homopolypurine/homopolypyrimidine sequence located in nucleic acid positions 1734–1754. Eleven base pairs of homopolypurine/homopolypyrimidine are at the 5'-end and eight base pairs at the 3'-end. Two complementary AT base pairs are inserted at nucleic acid positions 12 and 13 of the 21bp fragment (see FIG. 2). According to the base pair matching principles for triplex DNA, two complementary fragments of HBV DR genes (fragments III and IV) and a series of triplex forming oligonucleotides fragments (TFOs B11–B15) were synthesised. In TFOs B12-B15, the positions corresponding to the TT in the DR region fragment were taken by AA, GG, CC and TT, respectively so as to determine which bases better match the two A.T pairs and form a more stable triple base entity, and thereby form a triplex DNA with relatively high stability. By comparing the stability of triplex DNA formed by combination of TFOs B12–B15 and B11 with the fragment of the DR region, it can be seen if the eight bases at the 3'-end of TFOs B12–B15 can form triplex DNA with the fragment of the DR region. Furthermore, if two hetero-bases are inserted in the homopolypurine/homopolypyrimidine sequence of dsDNA, it can be seen whether these two bases can simultaneously form triplex DNA with target DNA.

I.B. Terminal Modification of TFO

TFOs B1–B5 and TFOs B11–B15 described above were modified by 3'-monophosphorylation.

I.C. Synthesis and Purification of TFOs

Oligonucleotides were synthesised on a DNA synthesiser (ABI391-EP, PE company) using the phosphoamidite method. The products were purified by PAGE.

I.C.1. Synthesis of 3'-OH Oligonucleotides

The synthesis of 3'-OH oligonucleotides was carried out using 0.2 $\mu$mol solid-phase column (Glen Research product) and the 0.2 $\mu$mol procedure on an ABI391EP DNA synthesiser.

I.C.2. Synthesis of 3'-monophosphorylated Oligonucleotide Derivatives

The synthesis of 3'-monophosphorylated oligonucleotides was carried out using 0.2 μmol 3'-phosphate solid-phase column (3'-phosphate CPG, product of Glen Research company, full name is 2-[2-(4,4'-Dimethoxytrityloxy) ethylsulfomyl] ethyl-succinoyl long chain alkylamino-CPG) and the analogous procedure as above.

I.C.3. The deoxyoligonucleotides synthesised for this experiment are listed below.

```
Fragment I:(SEQ ID NO:13)     5' CA TTC CTC CTC CTG CCT CC AC 3' 21nt

Fragment II:(SEQ ID NO:14)    3' GT AAG GAG GAG GAC GGA GG TG 5' 21nt

B1 (SEQ ID NO:1)5'       AAG GAG GAG GAT GGA GG 3' 17nt

B2 (SEQ ID NO:2)5'       AAG GAG GAG GAC GGA GG 3' 17nt

B3 (SEQ ID NO:3)5'       AAG GAG GAG GAA GGA GG 3' 17nt

B4 (SEQ ID NO:4)5'       AAG GAG GAG GAG GGA GG 3' 17nt

B5 (SEQ ID NO:5)5'       AAG GAG GAG GA   3'    11nt

B6 (SEQ ID NO:15)5'      AAG GAG GAG GAT TTT TTT T  3' 19nt

B1 (3'P) (SEQ ID NO:1)   5' AAG GAG GAG GAT GGA GGp 3' 17nt

B2 (3'P) (SEQ ID NO:2)   5' AAG GAG GAG GAC GGA GGP 3' 17nt

B3 (3'P) (SEQ ID NO:3)   5' AAG GAG GAG GAC GGA GGp 3' 17nt

B4 (3'P) (SEQ ID NO:4)   5' AAG GAG GAG GAC GGA GGp 3' 17nt

B5 (3"P) (SEQ ID NO:5)   5' AAG GAG GAG GAP 3'    11nt

Control:(SEQ ID NO:16)   5' GGG ATG CAG TGG TGG AAT TCC ACA 3'24nt

Fragment III: (SEQ ID NO:  5'  AA  TCT CCT CCC CCA ACT CCT CCC AG 3' 25nt
17)

Fragment IV:(SEQ ID NO:   3'  TT  AGA GGA GGG GGT TGA GGA GGG TC 5' 25nt
18)

B11 (SEQ ID NO:6)        5'  AGA GGA GGG GG 3' 11nt

B12 (SEQ ID NO:7)        5'  AGA GGA GGG GGA AGA GGA GGG 3' 21nt

B13 (SEQ ID NO:8)        5'  AGA GGA GGG GGG GGA GGA GGG 3   21nt

B14 (SEQ ID NO:9)        5'  AGA GGA GGG GGC CGA GGA GGG 3' 21nt

B15 (SEQ ID NO:10)       5'  AGA GGA GGG GGT TGA GGA GGG 3' 21nt

B11 (3"P) (SEQ ID NO:6)  5'  AGA GGA GGG GGp 3'   11nt

B12 (3"P) (SEQ ID NO:7)  5'  AGA GGA GGG GGA AGA GGA GGGp 3' 21nt

B13 (3"P) (SEQ ID NO:8)  5'  AGA GGA GGG GGG GGA GGA GGGp 3' 21nt

B14 (3"P) (SEQ ID NO:9)  5'  AGA GGA GGG GGC CGA GGA GGGp 3' 21nt

B15 (3"P) (SEQ ID NO:10) 5'  AGA GGA GGG GGT TGA GGA GGGp 3' 21nt
```

Example II. Binding of TFO to Target DNA

II.A. Method

II.A.1. Labeling and Purification of Oligonucleotide Fragments with $^{32}P$

To 50 pmol of oligonucleotide fragment I (or III) was added 50 μCi of [γ-$^{32}$P] ATP, 2 u of T4 nucleotide polymerase and 1 μl of 10×T4 Forward buffer. Double-distilled water was added to 10 μl, and the mixture incubated at 37° C. for 1 h. Then 4 μl was left on ice and the remaining 6 μl was mixed with 50 pmol of oligonucleotide fragment II (or IV), incubated for 5 min at 100° C., gradually annealed and then analysed on 15% non-denatured PAGE. Following autoradiography, bands of dsDNA comprising fragments I and II (or III and IV) were cut out. The gel strips containing the bands were mashed, 500 μl distilled water was added, and the mixture soaked overnight on a mixer. The gel and water mixture was filtered on a column containing glass wool to remove the pieces of gel. The radioactivity of the filtrate was measured, then unlabelled dsDNA fragment was added to a final concentration of 1 pmol/μl, and the mixture stored at −20° C.

II.A.2. Formation of Triplex DNA and PAGE Blocking Analysis

To 10 μl reaction mixture containing 0.1 μmol/L $^{32}$P-dsDNA fragments, 10 mmol/L Tris.HCl pH 7.5, 0.5 mmol/L Spermidine and 10 mmol/L $MgCl_2$, were added 0, 1, 2, 3, 4, 5, 6, and 7 μmol/L of different TFOs, respectively. The mixtures were incubated for 4 h in a 37° C. water bath, and then left on ice for 10 min. The products were run on 15% non-denatured PAGE at 100 volts and 4° C. for 4 h and the gels autoradiographed. The darkness of each band was analysed by a density scanner. The same electrophoresis conditions were used for analysis of the effect of external conditions on triplex DNA formation.

II.A.3. Calculation of the Association Constant (Ka), Disassociation Constant (Kd) and Change in Free Energy (ΔG) of Triplex DNA Formation The chemical equation for the binding of oligonucleotide with dsDNA is as follows: TFO+dsDNA=triplex DNA. Assuming that the starting concentrations of TFO and dsDNA are a and b, respectively, and the concentration of triplex DNA after reaching equilibrium is f, thus the concentration of TFO and dsDNA remaining after reaching equilibrium is (a–f) and (b–f), respectively. Therefore, $$Ka = \frac{f}{(a-f)(b-f)},$$

but when a>>f, a–f≅a, thus, $$Ka = \frac{f}{a(b-f)} \cdot \left(\frac{f}{b-f}\right) = Ka \times a.$$

Drawing a graph of $$\left(\frac{f}{b-f}\right)$$

against a gives a straight line where the slope is Ka.

$$Kd = \frac{1}{Ka},$$

ΔG=–RTlnKa, where R is the gas constant and T is the absolute temperature. Thus the change in free energy (ΔG) for the formation of triplex DNA can be calculated.

II.B. Results and Analysis

II.B.1. The Effect of TFO on the Two Homopolypurine/homopolypyrimidine Sequences in the Pre-S Gene of HBV II.B.1.a. Gel Block Analysis of Triplex DNA Formed From TFO and Labeled dsDNA Fragment of HBV Pre-S Gene A portion of 5'-end $^{32}$P-labelled fragment I oligonucleotide was annealed with fragment II, and after purification by PAGE, 32p-labelled oligonucleotide and $^{32}$P-labelled double strand DNA fragment from HBV pre-S gene were isolated. The synthesised oligonucleotides and $^{32}$P-labelled double strand DNA fragment from HBV pre-S gene were analysed by gel blocking. Except for the control oligonucleotide NC, the other synthetic oligonucleotides B1, B2, B3, B4, B5 and B6 disclosed by this invention formed triplex DNA with the HBV gene fragments (see FIG. 3).

II.B.1.b. The Equilibrium Constant, Disassociation Constant and Change in Free Energy for the Formation of Triplex DNA from TFOs and HBV Pre-S Gene Following the autoradiography scans, the concentrations of dsDNA (b–f) and triplex DNA (f) of dsDNA following equilibrium were calculated. Drawing a graph of $$\left(\frac{f}{b-f}\right)$$

against a gives a straight line where the slope is Ka (see graph 4). Following the calculation of Ka, Kd and ΔG were calculated as $$Kd = \frac{1}{Ka},$$

ΔG=–RTlnKa (see table 1).

TABLE 1

Thermodynamic parameters for triplex DNA formed by TFO and HBV pre-S gene fragments

|  | B1 | B2 | B3 | B4 | B5 | B6 |
|---|---|---|---|---|---|---|
| Ka (×10$^5$M$^{-1}$) | 6.97 | 4.57 | 6.75 | 7.71 | 0.91 | 1.68 |
| Kd (×10$^{-6}$M) | 1.44 | 2.19 | 1.48 | 1.30 | 11.0 | 5.95 |
| ΔG (–kcal/mol) | 8.42 | 8.16 | 8.4 | 8.48 | 5.71 | 7.53 |

According to the results, looking at the effect of the 17 bp fragment (3127–3143) in HBV pre-S gene, the 11 nucleic acids at the 5'-end and the five nucleic acids of the 3'-end of TFOs B1–B4 are all the same homopolypurines, which respectively can have an analogous effect on the 11 base pairs at the 5'-end and the five base pairs of the 3'-end of the target sequence. In oligonucleotide B6, only 11 nucleic acids of the 5'-end can bind target dsDNA to form triplex DNA, none of the eight polyT bases at the 3'-end can match the target dsDNA. The results are shown in FIGS. 3, 4 and table 1, where the amount of triplex DNA formed by TFO B6 and HBV pre-S gene fragment and the Ka value are clearly less than for oligonucleotides B1–B4, and are similar to B5. This indicates that the nucleic acids at the 5'-and 3'-ends of oligonucleotides B1–B4 can bind dsDNA to form triplex DNA.

The 11 nucleic acids at the 5'-end and the five nucleic acids at the 3'-end of TFOs B1–B4 are the same sequence of homopolypurines. Only position 12, which is T, C, A or G, respectively, changes. The different stabilities of triplex DNA formed by B1–B4 and the HBV pre-S gene fragment suggests which corresponding base in the third oligonucleotide strand can match when a single cytosine is inserted in the homopolypurine chain of target dsDNA. The results from triplex DNA formation and gel blocking analysis show that the triplex DNA formed by TFO B4 and the HBV pre-S gene fragment is the most stable. Hence, when a C is inserted in the homopolypurine chain of the target DNA, a matching G should be located in the homopolypurine TFO, to form a more stable GGC triple entity.

TFO B5 only has 11 nucleic acids, and TFOs B1–B4 have 17 nucleic acids. Although TFO B5 can form triplex DNA with the target sequence, the stability of the triplex is less than that formed from TFOs B1–B4. So, based on the same target dsDNA, the longer the TFO, the more stable the resulting triplex DNA. The length of oligonucleotide is a key factor in the stability of triplex DNA.

II.B.2. The Effect of TFO on the Two Similar Homopolypurine/homopolypyrimidine Sequences in the HBV DR Region II.B.2.a Gel Block Analysis of Triplex DNA Formation from TFO and Labeled Fragment of the HBV DR Region A portion of 5'-end $^{32}$P-labelled fragment III oligonucleotide was annealed with fragment IV, and after purification by PAGE, $^{32}$P-labelled oligonucleotide and $^{32}$P-labelled double strand DNA fragment from the HBV DR region were isolated. The synthesised oligonucleotides and $^{32}$P-labelled double strand DNA fragment from the HBV DR region were analysed by gel blocking. The synthetic oligonucleotides B11, B12, B13, B14 and B15 disclosed by this invention formed triplex DNA with the HBV DR region fragments (see FIG. 5).

II.B.2.b. The Equilibrium Constant, Disassociation Constant and Change in Free Energy for the Formation of Triplex DNA from Oligonucleotides and HBV Genes Following the autoradiography scans, the concentrations of dsDNA (b−f) and triplex DNA (f) of dsDNA following equilibrium were calculated. Drawing a graph of $$\left(\frac{f}{b-f}\right)$$

against a gives a straight line where the slope is Ka (see graph 6). Following the calculation of Ka, Kd and ΔG were calculated as $$Kd = \frac{1}{Ka},$$

ΔG=−RTlnKa (see table 2).

TABLE 2

Thermodynamic parameters for triplex DNA formed from TFO and HBV DR region gene fragments

|  | B11 | B12 | B13 | B14 | B15 |
|---|---|---|---|---|---|
| Ka ($\times 10^6 M^{-1}$) | 1.23 | 1.68 | 1.25 | 0.93 | 2.21 |
| Kd ($\times 10^{-7} M$) | 8.11 | 5.94 | 8.02 | 10.7 | 4.52 |
| ΔG (−kcal/mol) | 8.78 | 8.97 | 8.79 | 8.6 | 9.14 |

The 11 bp at the 5'-end and the 8 bp at the 3'-end in the 21bp gene fragment (1734−1754) in the HBV DR region are a sequence of homopolypurines/homopolypyrimidines. Two A.T base pairs are inserted in positions 1745 and 1746. The 11 homopolypurines bases of TFO B11 can bind the first homopolypurine/homopolypyrimidine fragment at the 5'-end of the target DNA. The homopolypurine nucleotide sequences in the 11 nucleotides at the 5'-end and in the eight nucleotides at the 3'-end of TFOs B12−B15 can respectively bind the two homopolypurine/homopolypyrimidine fragments of target dsDNA, and there are insertions of AA, GG, CC, and TT in the binding region. These base pairs bind HBV gene fragments to form triplex DNA with different stabilities. From these results it can be determined which bases in the third oligonucleotide strand should be used to match the corresponding two thymines in the homopolypurine sequence of the target dsDNA. Triplex DNA formation and gel blocking analysis showed that all TFOs B11−B15 can bind the target dsDNA and form triplex DNA. But their stabilities are different. The stability of triplex DNA formed from B13 and the target sequence is similar to that formed from B11, which indicates that TFO B13 only has eleven bases at the 5'-end that participate in triplex DNA formation. Furthermore, the stabilities of triplex DNA formed from TFO B15 and B12 and the target DNA is markedly higher than that formed from B11, which indicates that TFO B15 and B12 have 11.nucleic acids at the 5'-end and eight nucleic acids at the 3'-end involved in triplex DNA formation. Also, TT insertion has even less effect on the formation of triplex DNA involving the two homopolypurine/homopolypyrimidine fragments than does AA insertion. The stability of triplex DNA formed from TFO B14 and target DNA is less than the stability of that formed from TFO B11, implying the existence of a CC influences the stability of triplex formation. TFO B11 only has 11 nucleotides compared to the 21 of B15, and they can both bind the target sequence to form triplex DNA, but the stability of triplex DNA formed from B15 and the target DNA is markedly higher than that formed from TFO B11. Therefore, based on the same target dsDNA sequence, the longer the TFO sequence, the more stable the resulting triplex DNA. As for comparing the stability of triplex DNA formed from TFO B15 and the target HBV DR region sequence with that of the triplex DNA formed between TFO B4 and the pre-S gene target DNA, the former is more stable than the latter. This is because TFO B15 is longer than TFO B4, which also supports the idea that the longer the TFO, the more stable the triplex DNA.

Example III. The Effect on HBV Gene Expression of TFO B4(3'P) and B15 (3'P)

III.A. Procedure

III.A.1. HepG$_2$ Cells Co-transfected by Plasmid DNA (pl.2II) and TFO

HepG$_2$ cells were grown in 1×DMEM medium (containing 10% FCS) under 5% CO$_2$ at 37° C. The day before transfection, cells were inoculated into a 96 well plate and grown overnight. The medium was changed 2 h before transfection. Transfection solution A: 0.8 μg of plasmid pl.2II (provided by Prof. WANG Yuan, Institute of Biochemistry, Chinese Academy of Sciences, Shanghai) and different concentrations (0, 40, 80, 120, 160, and 200 pmol) of deoxyoligonucleotide TFOs B4(3'P) or TFO B15(3'P) (when the transfection volume is 20 μl, the concentration of deoxyoligonucleotide is 0, 2, 4, 6, 8 and 10 μmol/L, respectively), DMEM was added to 10 μl, and the solution mixed. Transfection solution B: 0.3 μl lipofectin was mixed with 9.7 μl DMEM and left at room temperature for 30 min. Solutions A and B were combined and left at room temperature for 30 min. Cells were washed twice with DMEM and added to the above transfection mixture (each sample was placed in six wells, the supernatants from three wells used for triplicate HBsAg determinations, and the other three wells were used for triplicate HBeAg determinations), and grown under 5% CO$_2$ at 37° C. for 5 h. Then 100 μl of DMEM containing 10% FCS was added per well and cultured for another 120 h. Finally, 100 μl of supernatant was used for determining HBsAg and HBeAg.

III.A.2. Determination of HBsAg and HBeAg in Cell Culture Supernatant

Samples of supernatant (100 μl per well) were added into a reaction plate coated with HBs antigen or HBe antigen. Two wells were positive controls for HBsAg or HBeAg, two wells were negative controls, and one well was a blank control. Except for the blank well, 100 μl of enzyme conjugate were added per well. The solutions were mixed well and the plate covered. The mixtures were incubated for 1h at 37° C., the supernatants were discarded, and the wells filled with a washing solution and washed for 20 seconds, spun dry, and this process was repeated five times. Next, 100 μl of substrate solution was added, the plate covered, incubated for 15 min at 37° C., and then 50 μl of stopping solution was added. The blank well was used to read '0' and the absorbance values $A_{492}$ from the solutions in each test well were read at 492 nm using a plate reader.

II.A.3. Calculation of the Inhibition Rate of HBsAg and HBeAg by TFO $$\text{Inhibition Rate} = \frac{A_{492} \text{ value without oligonucleotide added} - A_{492} \text{ value with oligonucleotide added}}{A_{492} \text{ value without oligonucleotide added}} \times 100\%$$

III.B. Results and Analysis

III.B.1. Timeline for the Effect on HBV Gene Expression in HepG$_2$ Cells Co-transfected by TFO and HBV Plasmid DNA HepG$_2$ cells were cultured in 12 well plates. Cells in each well were transfected with 10 μl of HBV gene plasmid p1.2II and 10 μmol/L of TFO B4(3'P) or TFO B15(3'P) in triplicate. Supernatant (200 μl) was taken every 12h, 100 μl of which was tested for HBeAg and the other 100 μl was tested for HBsAg. The average of three values was used (see FIGS. 7 and 8). After HepG$_2$ cells were transfected with HBV, if TFO was not added, HBeAg and HBsAg began expression on the second day, and the expression levels increased with time. But in HepG$_2$ cells co-transfected with 10 μmol/L of TFO B4(3'P) or TFO B15(3'P) and the HBV gene plasmid, the expression levels of HBeAg and HBsAg were markedly lower than when TFO was not added. This was especially the case when adding TFO B15(3'P), where inhibition of HBeAg and HBsAg expression was particularly prominent, and the expression of HBeAg and HBsAg increased very slowly. At the same time, the expression levels of HBeAg and HBsAg were slightly decreased in the control group (control oligonucleotide added). This may be caused by a decrease in the transfection efficiency of HBV DNA caused by oligonucleotides in the DNA transfection system, but the level of the decrease in HBeAg and HBsAg expression was much less than that caused by the inhibitory effect of TFOs.

II.B.2. Timeline for the Effect of TFO B15(3'P) in p1.2II Pre-Transfected HepG$_2$ on HBV Antigen Expression HepG$_2$ cells transfected with p1.2II were cultured on 12 well plates. TFO B15(3'P) was added to 10 μmol/L of final concentration per well and in triplicate. Every 10 h, 200 μl of supernatant was taken, of which 100 μl was tested for HBeAg and the other 100 μl was tested for HBsAg. The average of three values was used (see FIGS. 9 and 10). In HepG$_2$ cells transfected with the HBV gene, and to which no TFO was added, HBeAg and HBsAg started expression on the second day after transfection, and the expression levels gradually increased with time. But when 10 μmol/L of TFO B15(3'P) was present in the cell culture, HBsAg expression decreased markedly compared to the transfection where no TFO was present. But the effect on HBeAg expression was relatively small.

Example IV. The Inhibition by TFO of HBV Reproduction in HepG$_2$ cells

IV.A. Procedure

IV.A.1. Transfection of Plasmid DNA and TFO

HepG$_2$ cells were grown in 1×DMEM (containing 10% FCS) under 5% CO$_2$ at 37° C. One day before transfection, cells were cultured in 12 well plates overnight. The medium was changed 5 h before transfection. Transfection solution A: 10 μg of plasmid p1.2II, TFO in a final concentration of 10 μmol/L, add serum-free DMEM to 110 μl and mix. Transfection solution B: 6 μl of lipofectin, 114 μl serum-free DMEM, mix and leave for 30 min at room temperature. The cells were washed twice with DMEM and added to the above mixture of solution A and B (each sample was prepared in triplicate) and incubated in 5% CO$_2$ at 37° C. for 5h. Culture medium (DMEM containing 10% FCS, 2 ml) was added, and the cells were cultured under the above conditions for a further 5 days.

IV.A.2. DNA Extraction from Cells

After incubation with 10 μmol/L of TFO for 5 days, the cells were digested with pancreatin. The triplicate samples were combined and centrifuged at 3,000 g, 4° C. for 2 min. The cells were transferred into 1.5 ml Eppendorf tubes, TRIzol reagent (1.5 ml) was added, mixed well and left at room temperature for 5 min. Chloroform (0.2 ml) was added, vortexed for 15 sec and left at room temperature for 2–3 min. After centrifuging at 1,200 g, 4° C. for 15 min, the water phase was transferred into a fresh Eppendorf tube for total RNA extraction. Absolute ethanol (0.3 ml) was added to the middle and bottom organic phases and then mixed. After leaving at room temperature for 5 min, the mixture was centrifuged at 10,000 g for 5 min and the supernatant was discarded. The pellet was washed with 0.1 mol/L sodium citrate (1 ml), 10% ethanol, and then left at room temperature for 30 min with vortexing every 5 min. The mixture was then centrifuged at 10,000 g, 4° C. for 5 min, washed once more with 0.1 mol/L sodium citrate (1 ml) and 10% ethanol. The pellet was suspended in 75% ethanol and left at room temperature for 20 min with vortexing every 5 min. After centrifuging at 10,000 g, 4° C. for 5 min, the pellet was air dried and dissolved in 8 mmol/L NaOH solution (100 μl).

IV.A.3. Preparation of HBV Gene Probe

Intact, linear HBV DNA (3.2 kb) was prepared by digestion of plasmid p1.2II with BamHI nuclease, and purified by electrophoresis. HBV DNA probe was prepared by the random hexameric primer method (Fenzi Kelong Shiyan Zhinan-Molecular Cloning: A Laboratory Manual. 2$^{nd}$ Edition, J. Sambrook, E. F. Fritsch and T. Maniatis, ed. Translated by Dongyan JIN et al. Scientific Publishing House, 1986, p 502-4).

IV.A.4. Dot Blot Hybridisation of HBV DNA

Denatured HBV DNA was added to a nylon membrane by use of a vacuum filtration unit, crosslinked to the nylon by ultraviolet irradiation, and hybridised with $^{32}$P-probe for HBV DNA (Ref: Xiandai Fenzi Shengwuxue Shiyan Jishu—Experimental technique in modern molecular biology, Shendong LU ed, Higher Education Publishing, 1993, p 209–210).

IV.B. Results: Effect of TFO on the number of copies of HBV Gene in HepG$_2$ cells HepG$_2$ cells were cultured in 12 well plates and transfected with plasmid 1.2II carrying HBV gene and with 10 μmol/L of TFO B4(3'P) or TFO B15(3'P) in triplicate for 5 days. The transfected cells were digested, and the DNA extracted for dot blot hybridisation (see FIG. 11). It can be seen from the figure that the number of copies of HBV DNA in HepG$_2$ cells transfected with TFO B4(3'P) or TFO B15 (3'P) were less than the number produced in HepG$_2$ without TFO or with oligonucleotides that did not complement the HBV DNA (hydridisation dots were smaller in diameter and less dark). The results indicate that TFO can inhibit HBV reproduction.

What is claimed is:

1. A triplex forming oligonucleotide (TFO) selected from the group consisting of:

B1 (SEQ ID NO: 1) 5' AAG GAG GAG GAT GGA GG 3'

B2 (SEQ ID NO: 2) 5' AAG GAG GAG GAC GGA GG 3'

B3 (SEQ ID NO: 3) 5' AAG GAG GAG GAA GGA GG 3'

B4 (SEQ ID NO: 4) 5' AAG GAG GAG GAG GGA GG 3'

B12 (SEQ ID NO: 7) 5' AGA GGA GG GGA AGA GGA GGG 3'

B15 (SEQ ID NO: 10) 5' AGA GGA GGG GGT TGA GGA GGG 3'.

2. A triplex forming oligonucleotide as claimed in claim 1, wherein said TFO is 3' mono-phosphorylated.

3. A triplex forming oligonucleotide, as claimed in claim 2, which is capable of forming a triplex DNA structure when binding to two nearby fragments of homopolypurine and/or homopolypyrimidine DNA sequences.

4. A triplex forming oligonucleotide as claimed in claim 3, wherein said homopolypurine or homopolypyrimidine sequence is located in the DR region of HBV or in the pre-S gene promoter region of HBV.

5. A triplex forming oligonucleotide as claimed in claim 1, wherein said TFO is (SEQ ID NO: 4) 5' AAG GAG GAG GAG GGA GG 3' (B4) or a 3' mono-phosphorylated SEQ ID NO: 4.

6. A triplex forming oligonucleotide as claimed in claim 1, wherein said TFO is (SEQ ID NO: 10) 5' AGA GGA GGG GGT TGA GGA GGG 3' (B15) or a 3' mono-phosphorylated SEQ ID NO: 10.

7. A composition comprising a triplex forming oligonucleotide (TFO) selected from the group consisting of:

B1 (SEQ ID NO: 1) 5' AAG GAG GAG GAT GGA GG 3'

B2 (SEQ ID NO: 2) 5' AAG GAG GAG GAC GGA GG 3'

B3 (SEQ ID NO: 3) 5' AAG GAG GAG GAA GGA GG 3' or B4 (SEQ ID NO: 4) 5' AAG GAG GAG GAG GGA GG 3'

B12 (SEQ ID NO: 7) 5' AGA GGA GGG GGA AGA GGA GGG 3' or B15 (SEQ ID NO: 10) 5' AGA GGA GGG GGT TGA GGA GGG 3' and a pharmaceutically acceptable carrier.

8. A pharmnaceutical composition for the prevention or treatment of hepatitis B as claimed in claim 7, wherein said TFO is 3' mono-phosphorylated.

9. A composition as claimed in claim 7, wherein said TFO is selected from the group consisting of:

B1 (SEQ ID NO: 1) 5' AAG GAG GAG GAT GGA GG 3'

B2 (SEQ ID NO: 2) 5' AAG GAG GAG GAC GGA GG 3'

B3 (SEQ ID NO: 3) 5' AAG GAG GAG GAA GGA GG 3'

B4 (SEQ ID NO: 4) 5' AAG GAG GAG GAG GGA GG 3' and a pharmacuetically acceptable carrier.

10. A pharmaceutical composition as claimed in claim 9, further comprising an anti-sense sequence AsPS (SEQ ID NO: 12) 5' GGA GGC AGG AGG AGG AA 3' of pre-S region of HBV.

11. A composition as claimed in claim 10, wherein said TFO is (SEQ ID NO: 4) 5' AAG GAG GAG GAG GGA GG 3' (B4) or a 3' mono-phosphorylated SEQ ID NO: 4.

12. A composition as claimed in claim 7, wherein said TFO is selected from the group consisting of:

B12 (SEQ ID NO: 7) 5' AGA GGA GGG GGA AGA GGA GGG 3' or B15 (SEQ ID NO: 10) 5' AGA GGA GGG GGT TGA GGA GGG 3'.

13. A composition as claimed in claim 12, further comprising an anti-sense sequence AsDR (SEQ ID NO: 11) 5' TCT CCT CCC CCA ACT CCT CCC 3' of DR region of HBV.

14. A composition as claimed in claim 13, wherein said TFO is (SEQ ID NO: 10) 5' AGA GGA GGG GGT TGA GGA GGG 3' (B15) or a 3' mono-phosphorylated SEQ ID NO: 10.

* * * * *

SEQUENCE LISTING

<160> NUMBER OF SEQ ID NOS: 18

<210> SEQ ID NO 1
<211> LENGTH: 17
<212> TYPE: DNA

```
<213> ORGANISM: Artificial Sequence
<220> FEATURE:
<223> OTHER INFORMATION: Description of Artificial Sequence: Triplex
      forming oligonucleotide
<223> OTHER INFORMATION: This oligo may or may not be
      3'-monophosphorylated

<400> SEQUENCE: 1
aaggaggagg atggagg                                                    17

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Triplex
      forming oligonucleotide
<223> OTHER INFORMATION: This oligo may or may not be
      3'-monophosphorylated

<400> SEQUENCE: 2
aaggaggagg acggagg                                                    17

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Triplex
      forming oligonucleotide
<223> OTHER INFORMATION: This oligo may or may not be
      3'-monophosphorylated

<400> SEQUENCE: 3
aaggaggagg aaggagg                                                    17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Triplex
      forming oligonucleotide
<223> OTHER INFORMATION: This oligo may or may not be
      3'-monophosphorylated

<400> SEQUENCE: 4
aaggaggagg agggagg                                                    17

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: Triplex
      forming oligonucleotide
<223> OTHER INFORMATION: This oligo may or may not be
      3'-monophosphorylated

<400> SEQUENCE: 5
aaggaggagg a                                                          11

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: Triplex
      forming oligonucleotide
```

```
<223> OTHER INFORMATION: This oligo may or may not be
      3'-monophosphorylated

<400> SEQUENCE: 6
agaggagggg g                                                           11

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Triplex
      forming oligonucleotide
<223> OTHER INFORMATION: This oligo may or may not be
      3'-monophosphorylated

<400> SEQUENCE: 7
agaggagggg gaagaggagg g                                                21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Triplex
      forming oligonucleotide
<223> OTHER INFORMATION: This oligo may or may not be
      3'-monophosphorylated

<400> SEQUENCE: 8
agaggagggg ggggaggagg g                                                21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Triplex
      forming oligonucleotide
<223> OTHER INFORMATION: This oligo may or may not be
      3'-monophosphorylated

<400> SEQUENCE: 9
agaggagggg gccgaggagg g                                                21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Triplex
      forming oligonucleotide
<223> OTHER INFORMATION: This oligo may or may not be
      3'-monophosphorylated

<400> SEQUENCE: 10
agaggagggg gttgaggagg g                                                21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Triplex
      forming oligonucleotide
<223> OTHER INFORMATION: This oligo may or may not be
      3'-monophosphorylated

<400> SEQUENCE: 11
```
tctcctcccc caactcctcc c                                           21

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Triplex
      forming oligonucleotide
<223> OTHER INFORMATION: This oligo may or may not be
      3'-monophosphorylated

<400> SEQUENCE: 12
ggaggcagga ggaggaa                                                17

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: DNA
      Fragment

<400> SEQUENCE: 13
cattcctcct cctgcctcca c                                           21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: DNA
      Fragment

<400> SEQUENCE: 14
gtggaggcag gaggaggaat g                                           21

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Triplex
      forming oligonucleotide

<400> SEQUENCE: 15
aaggaggagg atttttttt                                              19

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: DNA Control

<400> SEQUENCE: 16
gggatgcagt ggtggaattc caca                                        24

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: DNA
      Fragment

<400> SEQUENCE: 17

```
aatctcctcc cccaactcct cccag                                          25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: DNA
      Fragment

<400> SEQUENCE: 18
ctgggaggag ttgggggagg agatt                                          25
```